United States Patent
Breneman

[19]

[11] Patent Number: 5,913,831
[45] Date of Patent: Jun. 22, 1999

[54] METHOD FOR TESTING REFLEXES USING ELECTROCARDIOGRAPH

[75] Inventor: James C. Breneman, 10571 Miller Dr., Galesburg, Mich. 49053

[73] Assignee: James C. Breneman, Galesburg, Mich.

[21] Appl. No.: 08/853,711

[22] Filed: May 9, 1997

[51] Int. Cl.[6] .................................................. A61B 19/00
[52] U.S. Cl. ..................... 600/553; 600/554; 600/587; 600/595
[58] Field of Search ................................ 600/553, 554, 600/587, 592, 595, 544

[56] References Cited

U.S. PATENT DOCUMENTS

| | | |
|---|---|---|
| 2,685,286 | 8/1954 | Torricelli . |
| 2,716,978 | 9/1955 | Torricelli . |
| 2,744,520 | 5/1956 | Torricelli . |
| 2,800,895 | 7/1957 | Torricelli . |
| 3,322,115 | 5/1967 | Richards . |
| 3,626,927 | 12/1971 | Breneman . |
| 3,734,082 | 5/1973 | Rawson et al. . |
| 3,739,768 | 6/1973 | Rieth . |
| 3,938,503 | 2/1976 | Vis . |
| 3,983,867 | 10/1976 | Case .......................................... 600/522 |
| 4,219,028 | 8/1980 | Lencioni, Jr. ............................ 600/544 |
| 5,012,820 | 5/1991 | Meyer ...................................... 600/595 |
| 5,044,366 | 9/1991 | Alt .............................................. 607/18 |
| 5,303,715 | 4/1994 | Nashner et al. ......................... 600/595 |
| 5,582,183 | 12/1996 | Breneman . |

*Primary Examiner*—Cary O'Connor
*Assistant Examiner*—Pamela L. Wingood
*Attorney, Agent, or Firm*—Price,Heneveld,Cooper, DeWitt & Litton

[57] ABSTRACT

A method for measuring and recording reflex response includes the steps of attaching an electrode to a first part of a test subject, connecting the electrode to an electrocardiograph, striking a body part of the test subject to elicit a reflex response, or stimulating a reflex by electrical current directed to the tendon, the current being similar to one generated by an electromyograph or a cardiac pacemaker, and measuring and recording the reflex response on the electrocardiograph. The method provides a simple, reliable procedure for producing accurate recordings of a patients reflex responses.

19 Claims, 4 Drawing Sheets

METHOD FOR TESTING REFLEXES USING ELECTROCARDIOGRAPH

BACKGROUND OF THE INVENTION

This invention relates to a method for testing reflex action of the Achilles tendons of a human subject to aid in the detection and diagnosis of various disorders and diseases.

It is well established that abnormal reflex action, such as exaggerated, attenuated, or slow reflex actions, can be a symptom indicative of certain diseases, neurological damage, or other physiological disorders. Because of well recognized correlations between abnormal human reflex action and certain medical disorders, and because reflex testing is a relatively inexpensive and nonintrusive procedure for quickly determining whether a patient might be afflicted with such medical disorders, physicians commonly rely on reflex testing as a screening technique during routine physical examination of a patient, with more specific testing generally being recommended to verify or determine the specific disorder afflicting those patients which exhibit abnormal reflexes. Reflex testing is also conveniently used to track the progress of patients which have been diagnosed with, and are being treated for, a particular disease or disorder which affects the patient's reflexes.

In its original and simplest form, reflex testing of the Achilles tendons of a patient was conducted by merely striking the patient's tendon with a reflex hammer and visually observing the reflex action of the patient. A physician could also supplement visual observations with tactile perceptions such as by holding the patient's foot before striking the patient's tendon to sense the force of the reflex actions. Even for highly skilled and experienced physicians, the reliability of detecting abnormal reflexes using manual striking technique and unaided visual and tactile perceptions was not always satisfactory. Moreover, such testing procedures are generally useless for tracking a patient's progress such as to determine whether the patient is responding favorably to a particular treatment. The deficiencies of simple reflex testing procedures including manual striking and sensory observations include the inherent difficulty of striking a patient's Achilles tendon in the same place with the same amount of force for each test, and the difficulty of judging whether a particular patient's reflex response deviates significantly from normal based on a comparison of the physician's visual and tactile observations of the patient's reflex response with the physician's memory of similar observations for a normal person.

In attempts to overcome the foregoing problems associated with manual reflex testing and unaided human sensory perception, and thereby improve the reliability and inherent utility of reflex testing, various devices have been developed for striking the Achilles tendon (or other selected portion of a patient's body) with an accurately reproducible, predetermined amount of force, and precisely at the desired position on the tendon, and various other devices have been developed for measuring and recording the reflex action induced by striking the Achilles tendon (or other portion of the patient's body). The problem of precisely striking a desired location on the Achilles tendon with an accurately reproducible amount of force has been solved, for example, by using a reflex hammer having a strike element, which is accurately positioned at the location on the tendon which is to be struck, and an impact member which is subjected to a predetermined, reproducible amount of momentum which is imparted to the strike element upon impacting therewith. For example, a simple, inexpensive reflex hammer which achieves reliable reproducability and utilizes an impact member which is dropped from a predetermined height above a strike element and impacts therewith is described in U.S. Pat. No. 3,626,927, issued to me on Dec. 14, 1971.

Known devices for measuring the reflex action of a patient in response to striking the Achilles tendon include simple mechanical devices, such as those comprising a lever, which is contacted by the patient's foot, and gears which mechanically link the lever with an indicating pointer operable over a dial to provide instantaneous readings of the amount of muscle contraction caused by striking the Achilles tendon. Such measuring devices do not provide a permanent record of the reflex action as a function of time, and are of very limited value for measuring the progress of a patient being treated for a particular disease or disorder which affects the reflexes.

Measuring devices which provide an electrical signal to a recording apparatus to generate a permanent record of reflex action as a function of time have generally been relatively complicated, expensive, and are less accurate than the simple mechanical measuring devices. Such measuring devices having a recordable electrical output include an electromagnetic field generator which is connected with a recording device to record fluctuations in the electromagnetic field caused by movement of a small permanent magnet attached to the patient's foot, which is generally positioned near the center of the electromagnetic field. The electromagnetic field measuring device does not provide an inherently accurate reading of muscle contraction and relaxation as a function of time because the disturbances caused by movement of a magnet through the electromagnetic field cannot be easily or directly correlated with the position of the magnet in the field. The device is also undesirable in view of recent findings which suggest that exposure to electromagnetic fields can be injurious to a person's health.

Another measuring device which is utilized to record reflex responses is a photoelectric detector. The photoelectric device is generally used by positioning the patient's foot so that it partially blocks a light beam directed at the photoelectric detector. The Achilles tendon of the patient is then struck causing the patient's foot to move further into the light beam, generating a change in the photocell voltage which is recorded. As with the electromagnetic field measuring device, the photoelectric device is relatively expensive and may not necessarily provide an accurate record of the position of the foot as a function of time after the Achilles tendon is struck, because the photoelectric detector is only responsive to the amount of light detected, which may not necessarily be directly related to the position of the foot in all cases. For example, errant light sources could interfere with the measurements, and the light beam directed at the photoelectric detector can be fully obscured before peak contraction of the muscle in response to striking the Achilles tendon, thereby making it difficult or impossible to accurately determine the time from peak contraction to when the muscle has relaxed to one-half of its peak contraction, a parameter which is commonly used to characterize reflex action, and used as an aid in diagnosing disease, prescribing treatment, and monitoring a patient's progress.

In view of the known reflex testing apparatuses, there is a need for an Achilles tendon reflex testing apparatus which is capable of inducing a reflex action in both left and right Achilles tendons, and which includes measuring devices for accurately measuring the reflex response of the muscles associated with the left and right Achilles tendons, respectively, and providing a recordable electrical output indicative of the measured reflex responses. Additionally, there is a need for a measuring device, for use with reflex testing apparatuses, which is capable of providing a recordable electrical output signal which is more accurately indicative of the reflexive muscle contraction and relaxation associated with striking an Achilles tendon, and which is relatively simple, reliable, and inexpensive as compared with known measuring devices which provide a recordable electrical signal indicative of a human reflex response.

SUMMARY OF THE INVENTION

This method involves attaching electrodes to the test subjects body, generally at the same location that a strike element would contact the test subject during conventional reflex testing, and an appropriate electrical impulse is generated and transmitted to the electrodes to stimulate the desired response.

The invention provides a method for quickly testing the reflex actions of a person in response to being struck upon the Achilles tendons. The invention utilizes a relatively simple, inexpensive reflex measuring device which provides a recordable electrical output. The measuring device is generally more accurate and more readily correlatable to the magnitude of the reflexive movement of a body part in response to the striking of an associated body part, than previous reflex measuring devices providing a recordable electrical output.

The invention involves a method of measuring and recording reflex response using a galvanometric measuring device. The method comprises attaching an electrode to a first part of a test object, electronically connecting the electrode to a galvanometric device, striking an associated part of the test subject's body to elicit a reflex response, and measuring and recording the reflex response on the galvanometric device.

In accordance with another aspect of the invention, a reflex response is stimulated using a device which can generate and deliver an electrical impulse to the tendon or other part of a test subject's body which is to be tested.

The method of the invention can be advantageously employed during routine physical examinations to provide a quick, easy, convenient, and direct comparison of the reflex responses of the left and right Achilles tendons under substantially identical circumstances, wherein the effects of heart rate, respiratory rate, and various other influences or reflex responses can be eliminated. Such direct comparisons may be extremely useful in the early detection of certain diseases, and could be of great utility to employers and insurance companies interested in quickly screening individuals to detect preexisting diseases or injury. The method is also of great utility in the measurement of a variety of reflex responses, including measurement of Achilles tendon reflex responses, as well as various other reflex responses.

These and other features, advantages and objects of the present invention will be further understood and appreciated by those skilled in the art by reference to the following specification, claims and appended drawings.

DETAILED DESCRIPTION OF PREFERRED EMBODIMENT

Figure 1:
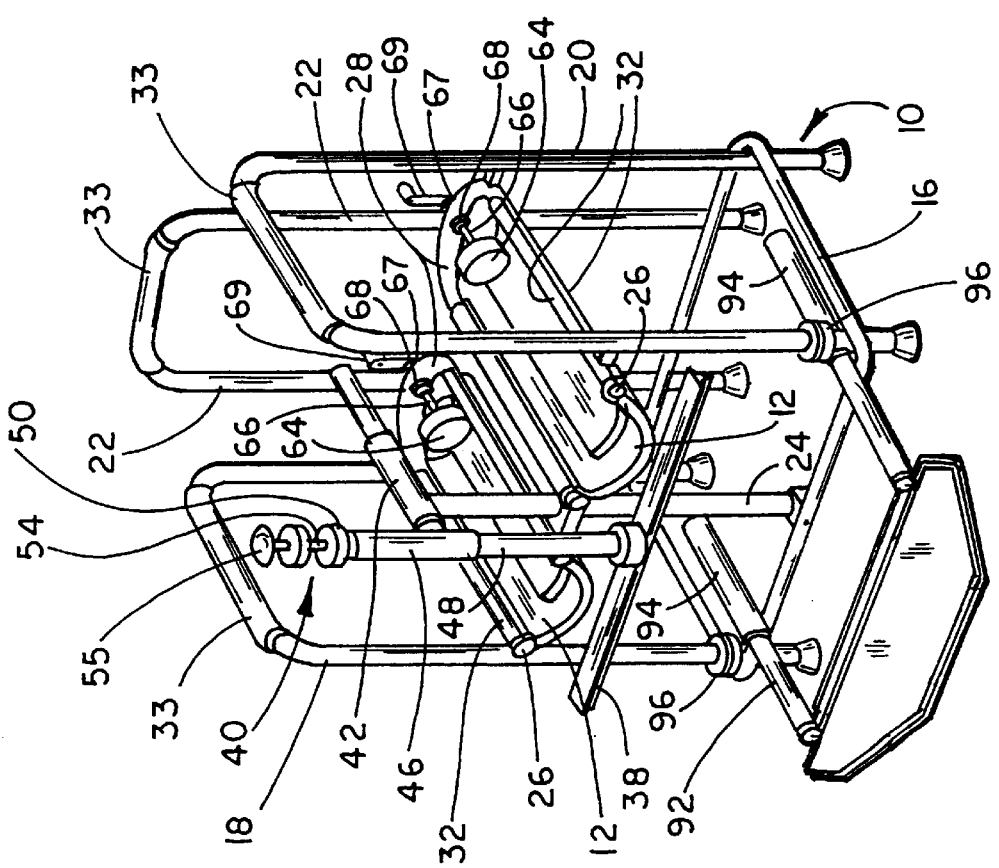
FIG. 1 is a perspective view of an Achilles tendon testing apparatus in accordance with the invention.
Figure 3:
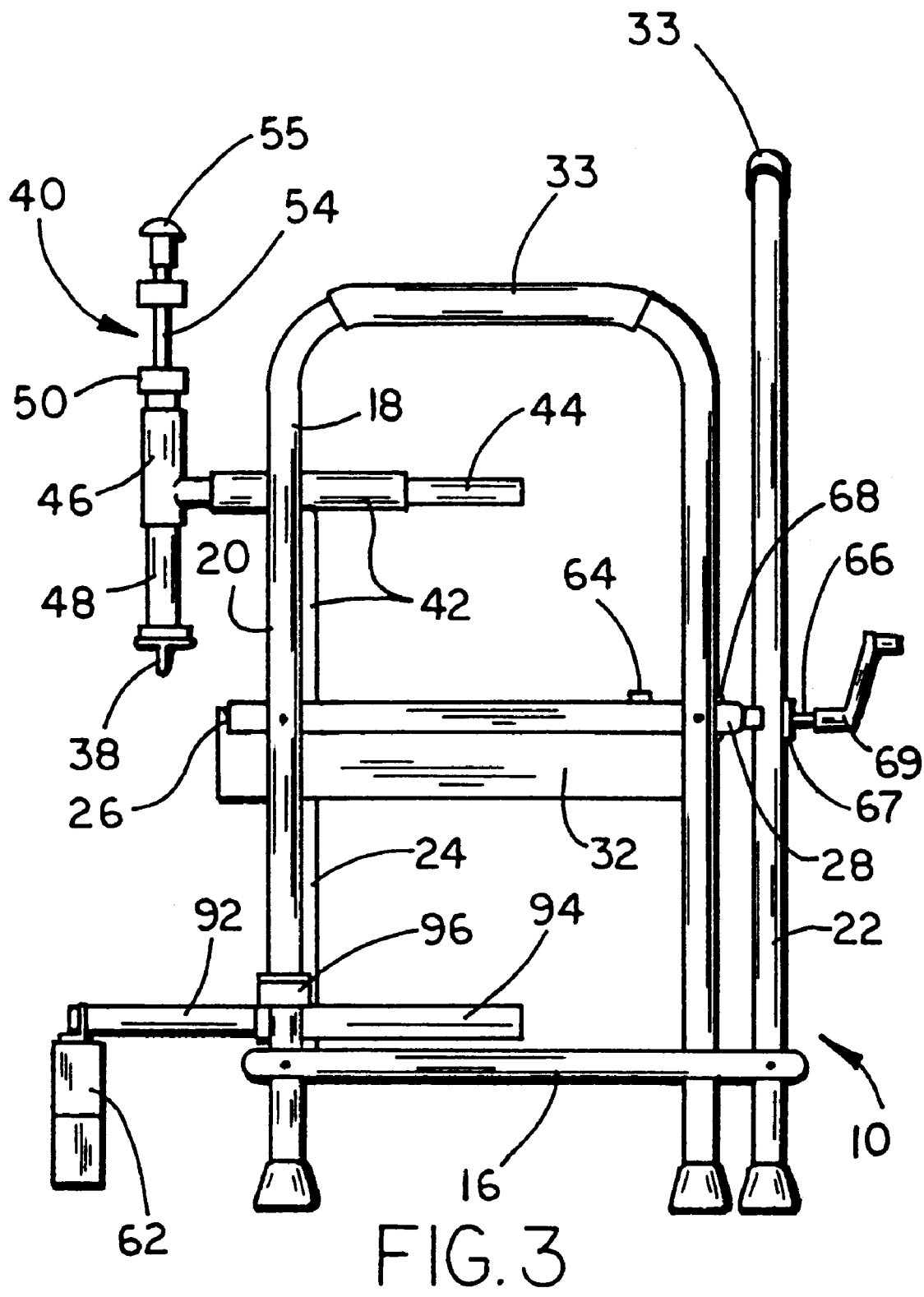
FIG. 3 is a side elevational view of the apparatus of FIG. 1.

An apparatus for testing the reflex action of a person's Achilles tendons, which is suitable for use in practicing the method of the invention is shown in FIGS. 1–4. With reference to FIG. 1, there is shown a reflex testing apparatus 10 having a support structure including a pair of spaced, parallel, substantially horizontally arranged leg supports 12 for the person's legs. The leg supports 12 are of sufficient length, and are contoured, to comfortably support a person's lower legs from the knee to about the ankles with the feet hanging unsupported over the back end of the leg supports 12. The leg supports 12 which have a substantially U-shaped transverse cross section, are mounted on a frame 14 which places the leg supports at an elevation above a floor which allows the person to easily kneel thereon from a standing position. The frame 14 is comprised of bent aluminum tubing, including a base 16, lateral stanchions 18, 20, 22 and brackets 26, 28. The stanchions 18, 20, 22 are bolted or otherwise fixedly secured to the base 16. The brackets 26, 28 are each bolted or otherwise fixedly secured to one of the lateral stanchions 18 and 20 respectively, to the front stanchion 22, and to the center leg 24.

Figure 2:
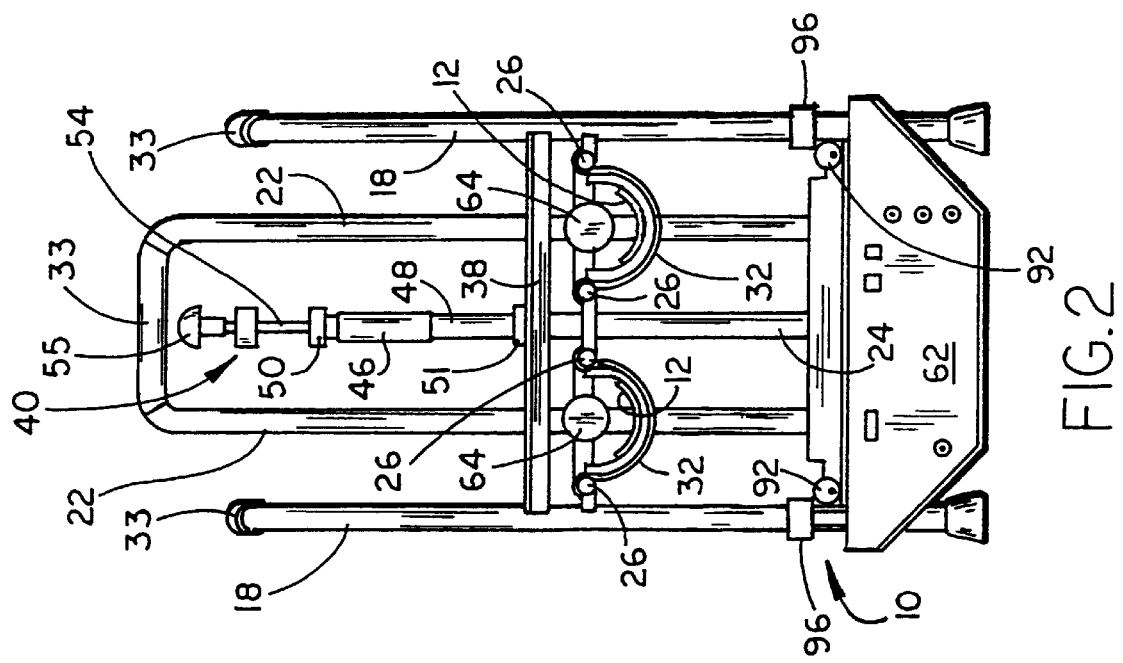
FIG. 2 is a front elevational view of the apparatus of FIG. 1.

The leg supports 12 are each comprised of a rigid underlying support member 32 and an overlying cushion 34 (FIGS. 1 and 2). The support member 32 is formed such as by bending or stamping a rigid metal sheet, such as an aluminum sheet, to form an elongate, U-shaped trough or channel having an inverted U-shaped lip portion 36 on each side thereof. The underlying support member 32 is preferably of suitable thickness, such as about $\frac{1}{16}$", so that the lip portions 36 can be received onto the tubular brackets 26, 28 and support the weight of a person without any significant strain or deflection of the support member 32 and without any need for bolting the support member 32 to the brackets, thereby eliminating upward projections from the brackets 26, 28 which could poke at a person mounting or dismounting the apparatus or snag a person's clothing. The stanchions 18, 20, 22 are each provided with hand grips 33 which can be used by the person being tested as that person is mounting, dismounting, or kneeling on the apparatus 10. The hand grips can be gripped by the patient to provide additional support, balance, and comfort to the person being tested while that person is kneeling on the apparatus.

Figure 4:
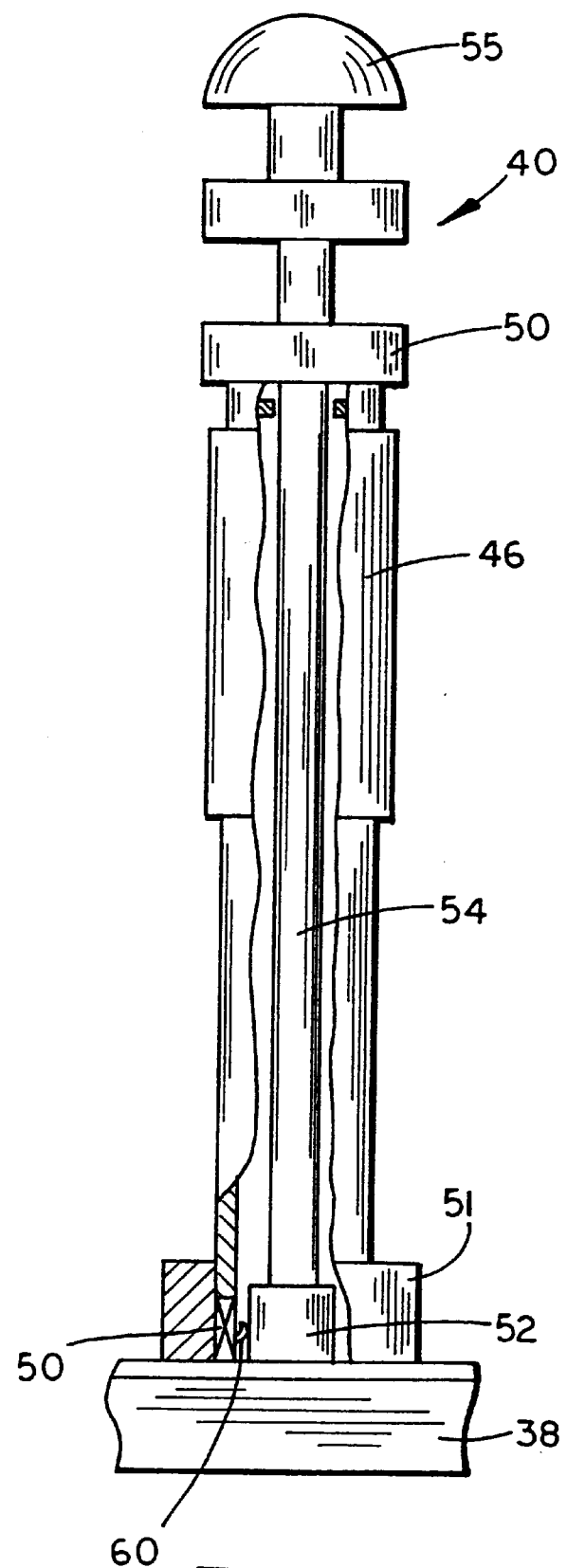
FIG. 4 is an exploded, fragmentary, elevational cross-sectional view showing detail of the reflex hammer used on the apparatus of FIG. 1.

An elongate, horizontal strike element 38 and hammer element 40 are supported on the center leg 24. More specifically, a tee 42 secured at the top of the center leg 24 receives a generally horizontal cantilever member 44 having at its rear end a tee 46 in which is received a generally vertical tube 48. The elongate, horizontal strike element 38 is secured at the bottom end of the vertical tube 48. The strike element 38 is of sufficient length to allow simultaneous striking of both left and right Achilles tendons of a person being tested. As illustrated, the strike element 38 has a continuous T-shaped transverse cross section. However, element 38 need not have a continuous cross section to achieve the objectives of the invention, it being possible to strike both tendons simultaneously with any element having a pair of strike surfaces or edges, each of which strikes a respective one of the tendons. The vertical tube 48, which is vertically movable within tee 46 includes a stop 50 attached at its top end which rests against the top edge of tee 46 to support the tube 48, hammer 40 and strike element 38 when the apparatus is not in use. Referring to FIG. 4, the hammer 40 includes an internal weight 52 secured to a plunger rod 54. The rod 54 has a handle 55 attached to its top end. The hammer 40, generally comprising weight 52, rod 54, and handle 55 falls through tube 48 which acts as a guideway directing the momentum of the hammer against the center (and center of mass) of the strike element to strike each tendon (left and right) with substantially identical force. At the bottom interior of tube 48 is an electrical switch 58 having a ball shaped button 60 which projects slightly into the interior of the hollow tube 48 and is engaged by weight 52 when the rod 54 is at its lowest position within tube 48. The switch 58 closes an electrical circuit when the rod 54 is at its lowest position within tube 48 to provide a signal to a microprocessor located within an electrical housing 62. The signal can be used to start a recorder or to indicate on a recording when the Achilles tendons were struck to induce a reflex action.

The strike element 38 and hammer 40 are mounted onto the center leg 24 in a manner which permits complete adjustability of the positioning of the strike element on a person's Achilles tendons to accommodate people of various proportions. In particular, tee 42 is rotatably attached to the top of leg 24 to allow lateral adjustment of the positioning of strike element 38, horizontal cantilever member 44 is axially slidable within tee 42 to allow adjustment of the strike element 38 along the longitudinal direction of the apparatus 10, and tube 48 is axially slidable within tee 46 to allow vertical adjustment of the position of strike element 38. As an aid to maintain proper positioning of the person kneeling on the leg supports 12 of apparatus 10, each leg support is provided with a knee stop 64 which is supported on a rod 66 passing through one of the brackets 26 or 28 and through one of the legs of stanchion 22. Rods 66 are threaded and carry internally threaded lock nuts 68 which allow the stops 64 to be approximately positioned along the length of the leg supports 12 to accommodate people of varying proportions so that the knees of the particular person being tested abut the stops 64 with the person's ankles generally overlapping the rear edge of the leg supports with the person's feet hanging freely from the leg supports.

Figure 5:
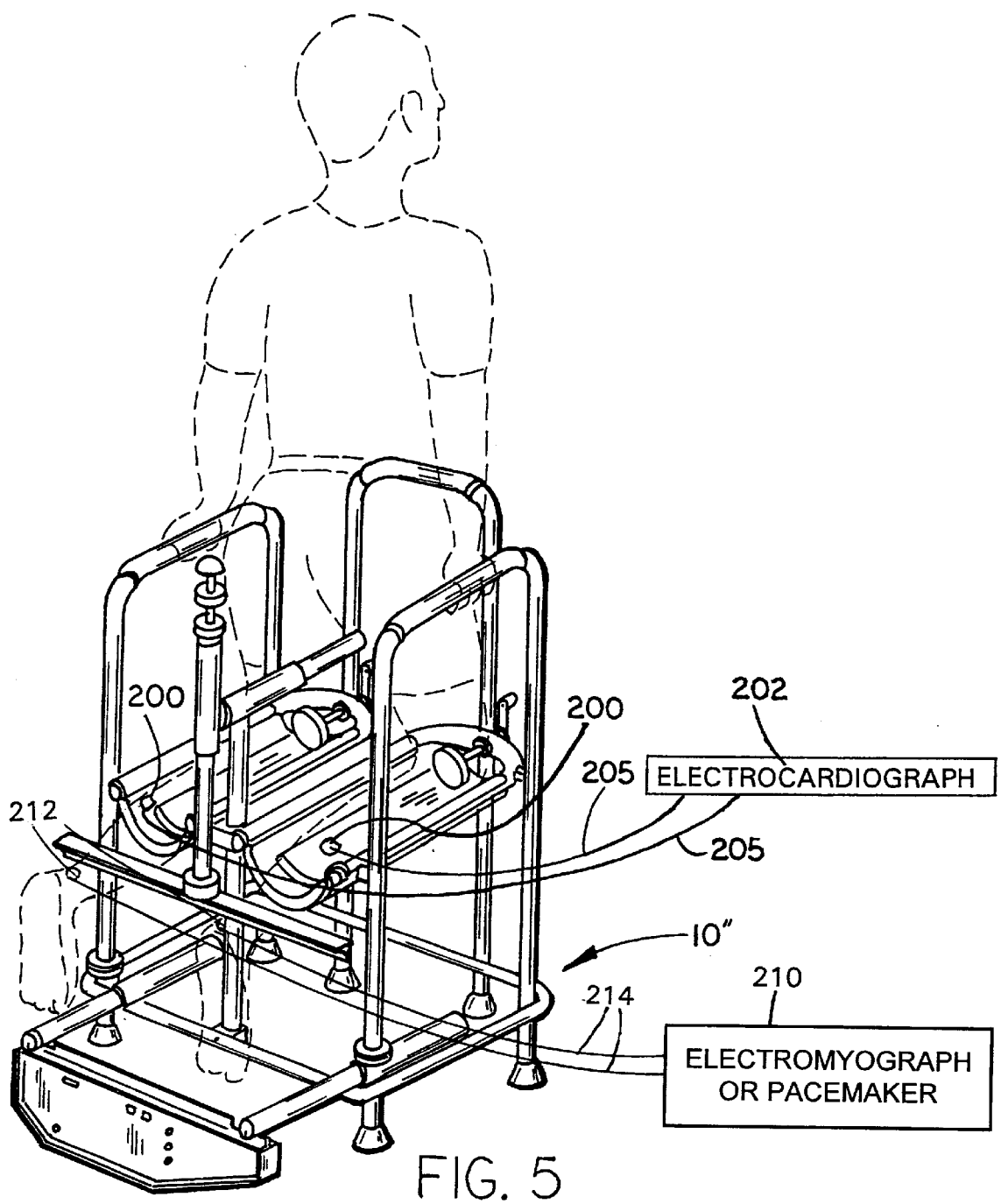
FIG. 5 is a perspective view of an alternative apparatus of the invention, wherein recording and measuring of the reflex response of a test subject is achieved using an electrocardiograph and electrodes suitably attached to the subject's calves.

The apparatus 10 is used by having a person (shown in phantam in FIG. 5) kneel on the leg supports 12 with their feet dangling freely over the back end thereof. The strike element 38 is then properly positioned on the Achilles tendons (both left and right) at the locations which are to be struck. Next, electrodes 200 are attached to the calves of the test subject and electrically connected to a galvanometric measuring device such as an electrocardiograph machine 202 (indicated schematically in FIG. 5) by an electrical conductor 205 so that when a reflex action is induced by striking the Achilles tendons, the electrocardiograph will track the movement of the feet and provide a recording indicative of the reflex response. After checking that electrodes 200 and electrocardiograph 202 are properly connected and functioning, the handle 55 is raised until the stop 56 engages ring 58 signifying that the hammer 40 has been raised a predetermined distance above strike element 38 or, alternatively, a predetermined distance above an anvil contained within tube 48 or disposed between tube 48 and strike element 38. The handle is then released causing the mass of the hammer 40 to accelerate under the influence of gravity through a predetermined change in elevation whereupon the hammer abruptly impacts on the strike element 38 or a part, such as an anvil, attached thereto, instantaneously transferring a predetermined and accurately reproducible amount of force or momentum to the strike element, which force or momentum is transmitted to both the left and right Achilles tendons. Because a strike element having rigidly connected strike surfaces or edges for each of the Achilles tendons is used, and because the impact between the strike element and the hammer element occurs substantially at the center of the strike element, each of the Achilles tendons is simultaneously struck with substantially identical force, thereby facilitating direct comparison of the reflex responses of the left and right Achilles tendons. Other types of hammers can also be used for impacting the strike element. For example, mass can be accelerated toward the strike element using a spring, solenoid or the like. At the moment the Achilles tendons are struck or immediately therebefore the hammer activates a switch which provides an electrical signal which can be used to trigger a recording device or indicate the start of the test, so that the duration of time between striking of the Achilles tendons and peak contraction of the muscles associated with the Achilles tendons, or other reflex characteristics, can be determined.

As an alternative to utilizing a strike element to stimulate a reflex response, an electrical impulse can be used instead, i.e., an electrical shock is delivered to the part of the test subjects body at which a reflex response to be elicited. For example, an electrical impulse generator such as an electromyograph 210 or cardiac pacemaker may be used to stimulate a reflex response of the Achilles tendons by positioning electrodes 212 generally over the Achilles tendons of a patient or test subject at the location where a strike element would normally contact the patient if a strike element were used. The electrodes are electrically connected to the electromyograph or cardiac pacemaker by electrical conductors 214. The appropriate current, voltage and the duration of the electrical impulse are selected to stimulate a reflex response comparable to a normal strike used to stimulate the desired reflex response. The amount of current and voltage used, and the duration of the electrical impulse are generally comparable or about the same as those used in electromyographic (EMG) or cardiac pacemaker techniques.

The above description is considered that of the preferred embodiments only. Modifications of the invention will occur to those skilled in the art and to those who make or use the invention. Therefore, it is understood that the embodiments shown in the drawings and described above are merely for illustrative purposes and are not intended to limit the scope of the invention, which is defined by the following claims as interpreted according to the principles of patent law, including the doctrine of equivalents.

The embodiments of the invention in which an exclusive property or privilege is claimed are defined as follows:

1. A method of measuring and recording reflex response comprising:

attaching an electrode to a first part of a test subject;

connecting the electrode to a galvanometric measuring device;

striking a body part of the test subject to elicit a reflex response; and measuring and recording the reflex response on the galvanometric measuring device.

2. The method of claim 1, wherein the test subject is supported in a kneeling position, the electrode is attached to the test subject's calf, and the Achilles tendon is struck to test the reflex response of the Achilles tendon.

3. The method of claim 2, wherein an electrode is attached to each of the calves of the test subject and is electrically connected to the galvanometric measuring device, and wherein both Achilles tendons are simultaneously struck to measure the reflex response of both Achilles tendons simultaneously.

4. The method of claim 1, wherein the galvanometric measuring device is an electrocardiograph.

5. A method of stimulating a reflex response in a test subject by delivering an electrical impulse to a part of a test subject's body for which a reflex response is to be tested, wherein an electrode is attached in proximity to a part of the test subject's body which is to be tested for a reflex response, the electrode is electrically connected to an electrical impulse generating device, and an electrical impulse is generated to cause an electrical shock to be delivered to the test subject from the electrode, wherein the electrical impulse generating device is an electromyograph or cardiace pacemaker.

6. A method of stimulating and measuring a reflex response in a test subject comprising:

delivering an electrical shock to a part of a test subject which is to be tested for reflex response; and measuring the reflex response using a galvanometric measuring device.

7. The method of claim 6, wherein the electrical shock is delivered to the test subject from an electrical impulse generating device electrically connected to an electrode attached to the test subject at a location in proximity to the part of the test subject's body which is to be tested.

8. The method of claim 7, wherein the electrical impulse generator is an electromyograph or cardiac pacemaker.

9. The method of claim 6, wherein the galvanometric measuring device is electrically connected to an electrode attached to the test subject's body.

10. The method of claim 9, wherein the galvanometric measuring device is an electrocardiograph.

11. A method of measuring and recording reflex response comprising:

attaching an electrode to a first part of a test subject;

connecting the electrode to a galvanometric measuring device;

stimulating a reflex response at a body part of the test subject; and measuring and recording the reflex response on the galvanometric measuring device.

12. The method of claim 11, wherein the step of stimulating a reflex response comprises striking the body part.

13. The method of claim 12, wherein the test subject is supported in a kneeling position, the electrode is attached to a test subject's calf, and an Achilles tendon is struck to test the reflex response of the Achilles tendon.

14. The method of claim 13, wherein an electrode is attached to each calf of the test subject and is electrically connected to the galvanometric measuring device, and wherein both Achilles tendons are simultaneously struck to measure the reflex response of both Achilles tendon simultaneously.

15. The method of claim 14, wherein the galvanometric measuring device is an electrocardiograph.

16. The method of claim 11, wherein the step of stimulating a reflex response comprises delivering an electrical shock to a part of a test subject which is to be tested for reflex response, and wherein the electrical shock is delivered to the test subject from an electrical impulse generating device electrically connected to an electrode attached to the test subject at a location in proximity to the part of the test subject's body which is to be tested.

17. The method of claim 16, wherein the electrical impulse generator is an electromyograph or cardiac pacemaker, and wherein the galvanometric measuring device is an electrocardiograph.

18. A method for directly comparing the reflex response of left and right Achilles tendons, comprising:

attaching first and second electrodes to a test subject's body in proximity to the test subject's left and right Achilles tendons respectively;

simultaneously delivering an electrical shock to the test subject's body from the first and second electrodes, to allow measurement of the reflex response of both Achilles tendons under substantially identical conditions; and measuring the reflex response of each of the Achilles tendons;

comparing the reflex responses of the left and right Achilles tendons.

19. The method of claim 18 in which an electromyograph or cardiac pacemaker is used for generating an electrical impulse and delivering the electrical shock to the test subject's body.

* * * * *